United States Patent
Blin

(12) 
(10) Patent No.: US 7,459,147 B2
(45) Date of Patent: Dec. 2, 2008

(54) COSMETIC COMPOSITION COMPRISING AT LEAST ONE HYDROPHILIC ORGANOPOLYSILOXANE, AT LEAST ONE HYDROCARBON OIL AND AT LEAST ONE SHORT HYDROCARBON ESTER

(75) Inventor: Xavier Blin, Paris (FR)

(73) Assignee: L'Oreal, Paris (FR)

( * ) Notice: Subject to any disclaimer, the term of this patent is extended or adjusted under 35 U.S.C. 154(b) by 152 days.

(21) Appl. No.: 10/875,556

(22) Filed: Jun. 25, 2004

(65) Prior Publication Data

US 2005/0043475 A1     Feb. 24, 2005

Related U.S. Application Data

(60) Provisional application No. 60/484,642, filed on Jul. 7, 2003.

(30) Foreign Application Priority Data

Jun. 30, 2003    (FR) .................................. 03 07873

(51) Int. Cl.
  A61K 8/25     (2006.01)
  A61K 8/37     (2006.01)
(52) U.S. Cl. ......................... 424/63; 424/401
(58) Field of Classification Search ........................ None
  See application file for complete search history.

(56) References Cited

U.S. PATENT DOCUMENTS

| | | | |
|---|---|---|---|
| 4,451,139 A | | 5/1984 | Yanagawa et al. |
| 5,068,960 A | | 12/1991 | Metzinger |
| 5,446,114 A | * | 8/1995 | O'Lenick, Jr. ............... 528/15 |
| 5,738,841 A | * | 4/1998 | Mellul et al. ................. 424/59 |
| 6,258,347 B1 | | 7/2001 | Sakuta et al. |
| 6,342,469 B1 | | 1/2002 | Lorant |
| 2001/0018044 A1 | | 8/2001 | Nakanishi et al. |
| 2001/0051686 A1 | | 12/2001 | Tabacchi et al. |
| 2003/0049215 A1 | * | 3/2003 | Calello et al. .................. 424/61 |

FOREIGN PATENT DOCUMENTS

| | | |
|---|---|---|
| EP | 437 216 A2 * | 1/1991 |
| EP | 548 694 A1 * | 12/1992 |
| EP | 0 548 694 B2 | 6/1993 |
| EP | 0 967 250 A1 | 12/1999 |
| EP | 1 112 734 A2 | 7/2001 |
| JP | 6-234858 | 8/1994 |
| JP | 7-233026 | 9/1995 |
| JP | 08-059430 | 3/1996 |
| JP | 10-130120 | 5/1998 |
| JP | 10-204316 | 8/1998 |
| JP | 10-330619 | 12/1998 |
| JP | 11-092358 | 4/1999 |
| JP | 2000-026233 | 1/2000 |
| JP | 2000-229814 | 8/2000 |
| JP | 2000-239117 | 9/2000 |
| JP | 2000-256121 | 9/2000 |
| JP | 2001-206815 | 7/2001 |
| JP | 2001-302489 | 10/2001 |
| JP | 2002-003334 | 1/2002 |
| JP | 2002-068934 | 3/2002 |
| JP | 2002-193729 | 7/2002 |
| WO | WO 97/16157 | 5/1997 |
| WO | WO 03/000223 A1 | 1/2003 |
| WO | WO 03/000233 A2 | 1/2003 |

* cited by examiner

*Primary Examiner*—Marc S Zimmer
(74) *Attorney, Agent, or Firm*—Oliff & Berridge, PLC

(57) ABSTRACT

The present invention relates to a cosmetic composition combining at least one organopolysiloxane possessing at least one hydrophilic radical with at least one hydrocarbon oil which is not compatible with the said organopolysiloxane, characterized in that it additionally comprises, as compatibilizing agent, an effective quantity of at least one hydrocarbon ester comprising less than 40 carbon atoms.

37 Claims, No Drawings

COSMETIC COMPOSITION COMPRISING AT LEAST ONE HYDROPHILIC ORGANOPOLYSILOXANE, AT LEAST ONE HYDROCARBON OIL AND AT LEAST ONE SHORT HYDROCARBON ESTER

This non-provisional application claims the benefit of French Application No. 03 07873 filed on Jun. 30, 2003 and U.S. Provisional Application No. 60/484,642 filed on Jul. 7, 2003.

The present invention relates to a cosmetic composition containing at least one organopolysiloxane comprising a hydrophilic unit, a hydrocarbon oil which is not compatible with the said organopolysiloxane and a compatibilizing agent.

For the purposes of the present invention, the cosmetic compositions constitute in particular make-up compositions such as powders, eye-shadows, foundations, concealers, lipsticks, make-up products for the body, mascaras, eyeliners or care compositions for the skin.

The use of hydrocarbon oils combined with organopolysiloxane derivatives in cosmetic, in particular make-up, compositions is known. In the case of cosmetic powders for example, a mixture of mineral and vegetable oils combined with fatty acid esters is generally used as binder, in order to obtain compositions which adhere well to the skin and are resistant to impact. As for the organopolysiloxane derivatives, they are generally incorporated into this type of binder in particular to provide smoothness. They also make it possible to improve the staying power of the foundation or lipstick compositions for example, and to obtain on the keratinous materials a film which is particularly homogeneous and which possesses good cosmetic properties.

Thus, it is advantageous to have cosmetic compositions comprising both organopolysiloxane derivatives and hydrocarbon oils.

However, a large number of silicone compounds are found to be incompatible with conventional hydrocarbon oils. This incompatibility can manifest itself in particular by phenomena of phase separation, precipitation or syneresis when these two types of compounds are brought into contact. A problem of heterogeneity in the composition therefore follows. This problem of incompatibility is particularly damaging in the case of cosmetic powders since they prevent the obtaining of a good dispersion of the pigments.

Various solutions have been proposed to try to compensate for this incompatibility. Thus, the document EP 0 548 694 proposes using in a cosmetic composition an organopolysiloxane modified with polyoxyalkylenes. The documents EP 1 112 734, EP 0 967 250 and WO 97/16157 describe cosmetic compositions in which the hydrocarbon oil and the silicone derivative considered are combined in particular with a volatile solvent of the linear or cyclic silicone type and paraffin compounds. The corresponding cosmetic compositions are described as having a better stability in terms of colour, transfer and migration.

However, the use of this type of volatile solvent poses in turn a few problems. First of all, it does not always prove to be sufficiently inert in relation to plastic materials constituting the articles for packaging the corresponding compositions. Moreover, it is not always compatible with a use in cosmetic formulations whose preparation requires a heating step. Finally, the incorporation of a volatile solvent generally adversely affects the properties of gloss and comfort of the corresponding cosmetic compositions. In particular, rapid drying of the applied formula frequently causes a sensation of dryness in the made-up area.

A need therefore remains for a composition which does not exhibit the disadvantages mentioned above, that is to say which is homogeneous and stable, endowed with good properties of non-transfer and non-migration, which does not dry and which does not pull the skin or the lips to which it is applied.

Unexpectedly, the inventors observed that it was possible to satisfy all these requirements, provided a specific compatibilizing agent is combined with these two types of compound.

More precisely, the present invention relates, according to one of its aspects, to a cosmetic composition combining at least one organopolysiloxane possessing at least one hydrophilic radical with at least one hydrocarbon oil which is not compatible with the said organopolysiloxane, characterized in that it additionally comprises, as compatibilizing agent, an effective quantity of at least one hydrocarbon ester comprising less than 40 carbon atoms.

According to a preferred variant of the invention, this ester is nonvolatile.

The invention also relates, according to another of its aspects, to a cosmetic method for caring for or making up the lips, the superficial body growths or the skin, comprising the application to the lips, the superficial body growths or the skin of a cosmetic composition in accordance with the invention.

Its subject is also, according to another of its aspects, the use of a composition in accordance with the invention for making up the skin, the lips or the superficial body growths.

The inventors have thus demonstrated that by combining an organopolysiloxane in accordance with the invention, an hydrocarbon oil, which is not compatible with the said organopolysiloxane, and a hydrocarbon ester comprising less than 40 carbon atoms, it is possible to obtain a cosmetic composition with sustained homogeneity and which exhibits excellent cohesion, but which also makes it possible to obtain a glossy deposit, which has good staying power and does not migrate.

The ester according to the invention is particularly advantageous insofar as it makes it possible to significantly reduce the quantity of volatile solvent, conventionally used, in particular to a value of less than 10% by weight, in particular of less than or equal to 5% by weight, or even to totally dispense therewith in a cosmetic composition in accordance with the present invention.

For the Purposes of the Present Invention:
- the expression "oil" is understood to mean any nonaqueous medium which is liquid at room temperature (25° C.) and at atmospheric pressure (760 mmHg),
- the expression "hydrocarbon ester" is understood to mean a hydrocarbon compound comprising at least one ester functional group,
- the expression "organopolysiloxane" is understood to mean a polymer comprising a polymeric backbone composed of siloxy repeating units which may be cyclic, linear or branched units, for example lower dialkylsiloxy units such as in particular dimethylsiloxy units,
- the expression "hydrophilic organopolysiloxane" is understood to mean an organopolysiloxane possessing at least one hydrophilic radical, the hydrophilic radical being grafted to one of the ends of the organopolysiloxane backbone or to the organopolysiloxane backbone,
- the expression "hydrophilic radical" is understood to mean a radical which confers hydrophilic properties on the organopolysiloxane. Examples of hydrophilic radicals are hydroxy, polyethyleneoxy, hydroxyl, carboxylate, sulphonate, sulphate, phosphate and amine,
- the expression "non-volatile" compound or medium is understood to mean any compound or medium being liable to stay on skin, lips or superficial body growths for several hours. A non volatile medium has in particular a non-zero vapour pressure, of less than 2×10−2 mmHg (2.66 Pa), at room temperature (25° C.) and at atmospheric pressure (760 mm Hg), the expression "not compatible" is understood to mean an incompatibility state manifesting itself in the presence of cloudiness or phase separation observed with the naked eye in a test-tube 1 to 2 cm in diameter containing hydrocarbon oil at 60° C. when organopolysiloxane is introduced at the scale of 10 or so, percents The esters in accordance with the invention which are more particularly non volatile may be monoesters, diesters or polyesters, and are more particularly monoesters, that is to say carrying a single ester functional group. These esters may be linear, branched or cyclic, saturated or unsaturated. Preferably, they are branched and saturated.

In particular, the hydrocarbon ester may correspond to the formula RCOOR' in which RCOO represents a fatty acid residue comprising from 2 to 28 carbon atoms, and R' represents a hydrocarbon chain containing from 1 to 28 carbon atoms. More particularly, groups R and R' are such that the corresponding ester is not volatile.

Those non volatile esters may be notably in $C_{10}$-$C_{25}$, and in particular in $C_{14}$-$C_{22}$. They may be selected among the esters of acids in $C_2$-$C_{18}$ and in particular, of alcohols in $C_2$-$C_{20}$ or polyols in $C_2$-$C_8$ or mixtures thereof.

Thus, the esters may be chosen from a nonlimiting list comprising the esters of neopentanoic acid such as isodecyl neopentanoate, isotridecyl neopentanoate, isostearyl neopentanoate, 2-octyldodecyl neopentanoate, the esters of isononanoic acid such as isononyl isononanoate, octyl isononanoate, isodecyl isononanoate, isotridecyl isononanoate, isostearyl isononanoate, but also the esters of isopropyl alcohol, such as isopropyl myristate, isopropyl palmitate, isopropyl stearate or isostearate, cetyl octanoate, tridecyl octanoate, 2-ethylhexyl 4-diheptanoate and palmitate, alkyl benzoate, polyethylene glycol diheptanoate, propylene glycol 2-diethyl hexanoate and mixtures thereof. The said ester may also be chosen from synthetic esters in particular of fatty acids such as purcellin oil, isopropyl myristate, ethyl palmitate, octyl stearate; the hydroxylated esters such as isostearyl lactate, octyl hydroxystearate, diisopropyl adipate, heptanoates, octanoates, decanoates of fatty alcohols and mixtures thereof.

Isononyl isononanoate, is most particularly suitable for carrying out the invention.

This or these hydrocarbon ester(s) may be used in the composition in an amount of 5 to 90%, in particular of 10 to 60% and in particular of 20 to 50% by weight relative to the total weight of the composition.

The hydrophilic organopolysiloxane used in the composition may be liquid or solid at room temperature.

The hydrophilic radical may be in particular a saturated or unsaturated hydrocarbon group optionally comprising one or more heteroatoms such as for example oxygen or sulphur, which hydrocarbon group may be substituted with at least one hydrophilic group. Examples of hydrophilic groups are in particular hydroxyl, carboxylic, carboxylate, thiol, amine, sulphonate, sulphate, phosphate, and/or hydroxypolyethyleneoxy functional groups.

More precisely, the hydrophilic radical may correspond to formula (II):

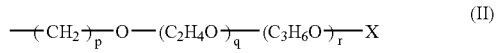

in which
p varies from 0 to 5, q varies from 0 to 100, r varies from 0 to 50, with p or q being different from zero,
the units ($C_2H_4O$) and ($C_3H_6O$) may be distributed randomly or in blocks, and
X is hydrogen or a $C_1$-$C_{10}$ alkyl radical, where appropriate substituted with one or more functional groups of the hydroxyl, thiol, amine, carboxylic, carboxylate, amide, phosphate, sulphate and sulphonate type.

In particular, p may vary from 1 to 5, q from 1 to 100 and r from 1 to 50. X may more particularly represent a hydrogen atom.

In particular, the organopolysiloxane in accordance with the invention may comprise as for hydrophilic radical at least one hydroxpolyalkylenoxy radical and in particular a hydroxypolyethylenoxy radical.

In particular, the organopolysiloxane according to the invention may correspond to formula (I):

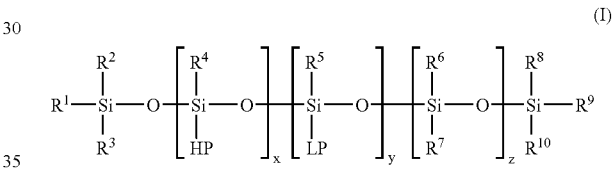

in which
$R^1$, $R^2$, $R^3$, $R^4$, $R^5$, $R^6$, $R^7$, $R^8$, $R^9$, and $R^{10}$ represent, independently of each other, a saturated or unsaturated, linear, branched or cyclic, $C_1$ to $C_6$ alkyl radical,
HP is a radical carrying at least one hydrophilic group as defined above,
LP is a lipophilic radical,
x varies from 1 to 5 000; y from 0 to 5 000; z from 0 to 5 000.

As regard LP radical, it may be chosen among branched, cyclic or linear $C_1$-$C_{40}$ alkyl radical, fluor atoms, aryl, aryloxy, hydrocarbylacyl $C_1$-$C_{40}$ and hydroxypropylenoxy.

According to a particular variant, the organopolysiloxane belongs to the polyethyleneglycol dimethicones family, and in particular may be chosen in the group comprising the copolyol diméthicone, in particular the copolyol cetyldiméthicone and derivatives thereof. The hydrophilic organopolysiloxane according to the present invention may be a product marketed under the brand Abil WE09 or Abil EM90 by the company DEGUSSA-GOLDSCHMIDT. The hydrophilic organopolysiloxane according to the present invention may be a product marketed under the reference KF-6017 by the company SHIN-ETSU.

The organopolysiloxane compound may be fully or partly fluorinated. In particular, the lower dialkylsiloxy groups may be substituted with one or more fluor atoms.

The organopolysiloxane may be present in an amount of 0.1 to 50%, in particular from 0.5 to 40%, and in particular from 1 to 30% by weight relative to the total weight of the composition.

Its viscosity may be comprised between 0.5 and 1 000 000 cst, in particular 25 to 600 000 cst and in particular 200 000 to 250 000 cst, at 25° C. measured according to the ASTM D-445 standard.

The hydrocarbon oil which can be used according to the invention may be apolar and/or nonvolatile. It is not compatible with the organopolysiloxane in the absence of the ester in accordance with the invention.

It may be chosen from oils of animal origin, such as perhydrosqualene, vegetable hydrocarbon oils such as liquid triglycerides of fatty acids of 4 to 24 carbon atoms such as heptanoic or octanoic triglycerides, sunflower, maize, soyabean, gourd, grapeseed, sesame, rapeseed, hazelnut, apricot, macadamia, castor, and avocado oils, triglycerides of caprylic/capric acids, jojoba oil, shea butter; linear or branched hydrocarbons of mineral or synthetic origin, such as paraffin oils and their derivatives, petroleum jelly, polydecenes, hydrogenated polyisobutenes; partly fluorinated hydrocarbon and/or silicone oils and mixtures thereof.

It may be chosen more particularly from hydrogenated or nonhydrogenated, nonvolatile hydrocarbon paraffins such as polydecene, polyisobutene, mineral oils, squalene and liquid polyalphaolefins, and may be in particular a hydrogenated isoparaffin of the polyisobutene type such as that marketed under the name Parleam.

The hydrocarbon oil may be present in an amount of 3.5 to 50%, in particular 4 to 40% and in particular 4 to 35% by weight relative to the total weight of the composition.

In general, the respective quantities in accordance with the invention of hydrophilic organopolysiloxane, of hydrocarbon oil and of hydrocarbon ester are chosen in a sufficient quantity to confer on the composition the expected properties in terms of stability, homogeneity, non-transfer, non-migration, gloss and comfort.

More particularly, the organopolysiloxane compound may be present in a proportion by mass equal to or less than that of the hydrocarbon oil. In other words, the weight ratio R defined by:

R=% by mass of organopolysiloxane/% by mass of hydrocarbon oil is less than 1, in particular varies from 0.01 to 0.7 and in particular from 0.1 to 0.5.

According to a particular variant of the invention, the composition combines a copolyol dimethicone, hydrogenated polyisobutene, in particular this marketed under the name Parleam by the company NIPPON OIL FATS, and isononyl isononanoate.

The composition may additionally contain at least one fatty substance different from the polar organopolysiloxane, incompatible hydrocarbon oil and hydrocarbon ester. This fatty substance may be chosen in particular from waxes, fatty substances which are pasty at room temperature, cosmetically and dermatologically acceptable oils and mixtures thereof.

The nature and the quantity of the waxes and of the pasty fatty substances are generally adjusted as a function of the desired mechanical and textural properties.

The additional fatty substance(s) of the composition may represent from 0.1% to 90% of the total weight of the composition, preferably from 5 to 60% and better still from 10 to 50%.

The composition according to the invention may also contain few volatile oils, and in particular less than 10% of the total weight of the composition, in particular less than 5%, even better less than 2%, and in particular is free of any volatile oil.

The composition according to the invention may additionally contain at least one inert particulate phase and in particular a filler which is in particular inert, absorbent or otherwise.

This inert particulate phase may represent from 0.1 to 30% and better still from 2 to 25% and better still from 10 to 20% by weight of the total weight of the composition.

The composition of the invention may also comprise at least one colouring matter such as for example one or more pulverulent compounds and/or one or more fat-soluble colorants, in particular in an amount of 0 to 70% of the total weight of the composition and in particular 0.01 to 70%. The pulverulent compound(s) may be chosen from pigments, pearlescent agents, which are customarily used in cosmetic or dermatological compositions and mixtures thereof. The pulverulent colouring compounds may represent up to 50% of the total weight of the composition, for example from 0.01 to 50% and better still from 1 to 40% by weight relative to the total weight of the composition.

The composition of the invention may additionally contain one or more cosmetic or dermatological active agents such as those conventionally used.

As cosmetic or dermatological active agents which can be used in the composition of the invention, there may be mentioned moisturizers, vitamins, essential fatty acids, sphingolipids, sunscreens, soothing agents (Bisabolol, for example). These active agents are used in the usual quantity for persons skilled in the art and in particular at concentrations of 0 to 20% and in particular 0.001 to 20% and better still 0.1 to 5% by weight relative to the total weight of the composition. The composition according to the invention may further comprise, depending on the type of application envisaged, the conventional constituents used in the fields considered, which are present in a quantity appropriate for the desired galenic form.

The composition may additionally comprise any additive customarily used in such compositions, such as thickeners (hectorite modified with distearyldimethylammonium chloride for example known under the name Bentone®), antioxidants, perfumes, preservatives, surfactants, fat-soluble polymers. Of course, persons skilled in the art will be careful to choose this or these optional additional compounds, and/or their quantity, such that the advantageous properties of the composition according to the invention are not, or not substantially, impaired by the addition envisaged.

The compositions according to the invention may be prepared in the customary manner by a person skilled in the art. They may be provided in the form of a cast product and for example in the form of a stick or baton, or in the form of a dish which can be used by direct contact or with a sponge or alternatively in a boiling pan. In particular, they find application as cast foundation, blusher or eye-shadow, lipstick, care base or balm for the lips, concealer product, eyeliner and/or mascara. They may also be provided in the form of a soft paste or a gel, or a cream which is fluid to a greater or lesser degree. They may also constitute foundations or lipsticks or lip gloss, antisun products or skin colouring products.

The compositions of the invention are advantageously anhydrous, that is to say that they may contain less than 5% of water relative to the total weight of the composition. They may then be provided in particular in the form of an oily gel, an oily liquid, a paste or a stick or in the form of a vesicular dispersion containing ionic and/or nonionic lipids.

They may also be provided in the form of a simple or multiple emulsion with an oily or aqueous continuous phase, an oily dispersion in an aqueous phase by virtue of vesicles containing ionic and/or nonionic lipids.

These galenic forms are prepared according to the customary methods of the fields considered.

The compositions for topical application may constitute in particular a cosmetic or dermatological composition for protecting, treating or caring for the face, for the neck, for the hands or for the body (for example a care cream, an antisun oil, a body gel), a make-up composition (for example a make-up gel, a cream or a stick) or a composition for artificial tanning of the skin or for protecting the skin.

In particular, a composition according to the invention may be provided in the form of a foundation, a blusher or an eye-shadow, a lipstick, a care base or balm for the lips, a concealer product, an eyeliner and/or a mascara.

The composition according to the invention may be used in a method for caring for the lips, the skin or the superficial body growths consisting in applying such a composition to the lips, the skin or the superficial body growths.

The composition may be used for making up the skin, the lips or the superficial body growths.

The invention is illustrated in greater detail in the following examples. The percentages are percentages by mass. The names of some of the ingredients are given as a CTFA name.

EXAMPLE 1

This example demonstrates the efficacy of an ester in accordance with the invention as a compatibilizing agent.

In a hydrogenocarbonated fatty phase made of hydrogenated polyisobutene (sold under the reference Parleam by Nippon Oil Fats) representing 60% by weight of the composition, there is dispersed 10% by weight of a fluorinated ethoxylated silicone (copolyol diméthicone) (marketed under the reference KF 6017 by Shin-Etsu) in the presence of 30% by weight of isononyl isononanoate. A transparent and colourless stabilized homogeneous mixture is obtained.

When the same mixture is reproduced in the absence of isononyl isononanoate, a cloud and a phase separation are observed at 60° C.

EXAMPLE 2

A lipstick formulation having the following composition was prepared partly using the compounds of Example 1.

|  | % by weight |
|---|---|
| Phase A: | |
| Hydrogenated polyisobutene (Parleam) | 36 |
| Isononyl isononanoate | 30 |
| Polyethylene wax (MW 500) | 15 |
| Dimethicone copolyol | 10 |
| Phase B: | |
| Pigments | 8.8 |
| Phase C: | |
| Fragrance | 0.2 |

The glossy stick obtained has an improved staying power in the presence of the ester and surfactant combination, and in particular a reduced migration.

EXAMPLE 3

The formulation of Example 2 was tested in comparison with a formulation not containing the polyol dimethicone and isononyl isononanoate combination.

The migration stability results are presented below in Table I

| FORMULA | EXAMPLE 2 | CONTROL |
|---|---|---|
| Running into the fine lines (at 1 hour) | 2.0 | 5.6 |

A substantial improvement is noted in terms of migration. The formulation in accordance with the invention exhibits practically no running into the fine lines at 1 hour compared with the formulation of the controls.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An anhydrous cosmetic composition combining at least one partly or completely fluorinated organopolysiloxane possessing at least one hydrophilic radical with at least one hydrocarbon oil which is not compatible with the said organopolysiloxane, wherein said oil is present in an amount of at least 3.5% by weight relative to the total composition, and additionally comprises, as compatibilizing agent, an effective quantity of at least one hydrocarbon monoester comprising from 10 to 25 carbon atoms.

2. Composition according to claim 1, wherein the hydrocarbon monoester is nonvolatile.

3. Composition according to claim 1, wherein the hydrocarbon monoester corresponds to the formula RCOOR' in which RCOO represents a carboxylic acid residue comprising from 2 to 18 carbon atoms, and R' represents a hydrocarbon chain containing from 1 to 20 carbon atoms.

4. Composition according to claim 1, wherein the hydrocarbon monoester is in $C_{14}$-$C_{22}$.

5. Composition according to claim 1, wherein the said monoester is chosen among synthetic esters of fatty acids, hydroxylated esters, neopentanoïc acid esters, isononanoïc acid esters, isopropylic alcohol esters, and mixtures thereof.

6. Composition according to claim 5, wherein the said monoester is chosen among purcellin oil, isopropyl myristate, ethyl palmitate, isostearyl lactate, heptanoates, octanoates, decanoates of fatty alcohols; isodecyl neopentanoate, isotridecyl neopentanoate, isostearyl neopentanoate, 2-octyldodecyl neopentanoate, isononyl isononanoate, octyl isononanoate, isodecyl isononanoate, isotridecyl isononanoate, isopropyl palmitate, isopropyl stearate or isostearate, cetyl octanoate, tridecyl octanoate, alkyl benzoate, and mixtures thereof.

7. Composition according to claim 6, wherein the said monoester is isononyl isononanoate.

8. Composition according to claim 1, wherein the said monoester is present in an amount of 5 to 90% by weight relative to the total weight of the composition.

9. Composition according to claim 8, wherein the said monoester is present in an amount of 10 to 60% by weight relative to the total weight of the composition.

10. Composition according to claim 9, wherein the said monoester is present in an amount of 20 to 50% by weight relative to the total weight of the composition.

11. Composition according to claim 1, wherein the hydrophilic radical of the organopolysiloxane is a saturated or unsaturated hydrocarbon group comprising one or more heteroatoms.

12. Composition according to claim 11, wherein said heteroatom is chosen among oxygen or sulphur.

13. Composition according to claim 11, wherein said saturated or unsaturated hydrocarbon group is substituted with at least one hydrophilic group.

14. Composition according to claim 13, wherein the hydrophilic group is chosen from hydroxyl, carboxylic, carboxylate, thiol, amine, sulphonate, sulphate, phosphate and hydroxypolyethyleneoxy functional groups.

15. Composition according to claim 1, wherein the organopolysiloxane carries at least one hydrophilic radical which corresponds to formula (II):

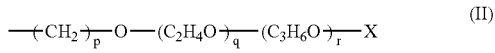

in which
p varies from 0 to 5, q varies from 0 to 100, r varies from 0 to 50, with p or q being different from zero,
the units ($C_2H_4O$) and ($C_3H_6O$) may be distributed randomly or in blocks, and
X is hydrogen or a $C_1$-$C_{10}$ alkyl radical.

16. Composition according to claim 15, wherein said X being $C_1$-$C_{10}$ alkyl radical is substituted with one or more functional groups chosen among hydroxyl, thiol, amine, carboxylic, carboxylate, amide, phosphate, sulphate and sulphonate.

17. Composition according to claim 1, wherein the partly or completely fluorinated organopolysiloxane carries at least one hydroxypolyethylenoxy radical.

18. Composition according to claim 1, wherein the partly or completely fluorinated organopolysiloxane corresponds to a fluorinated organopolysiloxane of the following general formula (I):

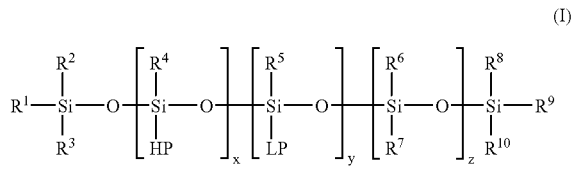

in which
$R^1$, $R^2$, $R^3$, $R^4$, $R^5$, $R^6$, $R^7$, $R^8$, $R^9$ and $R^{10}$ represent, independently of each other, a saturated or unsaturated, linear, branched or cyclic, $C_1$ to $C_6$ alkyl radical, and at least one of $R^6$ or $R^7$ is substituted with one or more fluor atoms,
HP is a radical carrying at least one hydrophilic group,
LP is a lipophilic radical,
x varies from 1 to 5 000; y from 0 to 5 000; z from 0 to 5000.

19. Composition according to claim 18, wherein the hydrophilic group of the organopolysiloxane is chosen from hydroxyl, carboxylic, carboxylate, thiol, amine, sulphonate, sulphate, phosphate and hydroxypolyethyleneoxy functional groups.

20. Composition according to claim 1, wherein the partly or completely fluorinated organopolysiloxane is a fluorinated derivative of an organopolysiloxane chosen from polyethylene glycol dimethicones.

21. Composition according to claim 1, wherein the partly or completely fluorinated organopolysiloxane is a fluorinated derivative of an organopolysiloxane chosen from copolyol dimethicones.

22. Composition according to claim 21, wherein said copolyol dimethicones is chosen from copolyol cetyl diméthicone and derivatives thereof.

23. Composition according to claim 1, wherein the organopolysiloxane is present in an amount of 0.1 to 50% by weight relative to the total weight of the composition.

24. Composition according to claim 23, wherein the organopolysiloxane is present in an amount of 0.5 to 40% by weight relative to the total weight of the composition.

25. Composition according to claim 24, wherein the organopolysiloxane is present in an amount of 1 to 30% by weight relative to the total weight of the composition.

26. Composition according to claim 1, wherein the hydrocarbon oil is apolar.

27. Composition according to claim 1, wherein the hydrocarbon oil is nonvolatile.

28. Composition according to claim 1, wherein the hydrocarbon oil is chosen from oils of animal origin, vegetable hydrocarbon oils linear, or branched hydrocarbons oils of mineral or synthetic origin.

29. Composition according to claim 28, wherein the hydrocarbon oil is chosen from perhydrosqualene, liquid triglycerides of fatty acids of 4 to 24 carbon atoms, heptanoic or octanoic triglycerides, sunflower, maize, soya-bean, gourd, grapeseed, sesame, rapeseed, hazelnut, apricot, macadamia, castor, and avocado oils, triglycerides of caprylic/capric acids, jojoba oil, shea butter; paraffin oils and their derivatives, petroleum jelly, polydecenes, hydrogenated polyisobutenes; partly fluorinated hydrocarbon oils and mixtures thereof.

30. Composition according to claim 29, wherein the hydrocarbon oil is an isoparaffin of the hydrogenated polyisobutene type.

31. Composition according to claim 1, wherein the hydrocarbon oil is present in an amount of 3.5 to 50% by weight relative to the total weight of the composition.

32. Composition according to claim 31, wherein the hydrocarbon oil is present in an amount of 4 to 40%, by weight relative to the total weight of the composition.

33. Composition according to claim 32, wherein the hydrocarbon oil is present in an amount of 4 to 35% by weight relative to the total weight of the composition.

34. Composition according to claim 1, wherein it additionally comprises at least one filler and/or one colouring matter.

35. Composition according to claim 1, wherein it is provided in the form of a foundation, a blusher or an eye-shadow, a lipstick, a care base or balm for the lips, a concealer product, an eyeliner and/or a mascara.

36. Method for the cosmetic treatment of or for making up the skin, the lips or the superficial body growths comprising the application to the lips, the skin or the superficial body growths of a composition according to claim 1.

37. Method for obtaining a skin, lips or superficial body growth make-up comprising preparing a composition according to claim 1.

* * * * *